US00PP23432P2

(12) United States Plant Patent
Hanes

(10) Patent No.: US PP23,432 P2
(45) Date of Patent: Feb. 26, 2013

(54) ***PETUNIA* PLANT NAMED 'PEHY0004'**

(50) Latin Name: *Petunia hybrida*
Varietal Denomination: PEHY0004

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,383

(22) Filed: Oct. 17, 2011

(51) Int. Cl.
*A01H 5/00* (2006.01)

(52) U.S. Cl. ..... Plt./356.1

(58) Field of Classification Search ..... Plt./356.1
See application file for complete search history.

*Primary Examiner* — Annette Para
(74) *Attorney, Agent, or Firm* — Joshua L. Price

(57) ABSTRACT

A new *Petunia* plant named 'PEHY0004' particularly distinguished by the small red-purple bi-colored flowers, medium green foliage, initially semi-compact and then an outwardly spreading plant habit with good field performance.

1 Drawing Sheet

Latin name of the genus and species of the plant claimed: *Petunia hybrida.*

Varietal denomination: 'PEHY0004'.

BACKGROUND OF THE NEW PLANT

The present invention comprises a new *Petunia*, botanically known as *Petunia hybrida*, and hereinafter referred to by the variety name 'PEHY0004'.

'PEHY0004' is a product of a planned breeding program. The new cultivar has small red-purple bi-colored flowers, medium green foliage, initially semi-compact and then an outwardly spreading plant habit with good field performance.

'PEHY0004' originated from a hybridization made in August 2007 in a controlled breeding environment in Gilroy, Calif. The female parent was the proprietary, unpatented plant designated '1749-1' with lavender flowers, darker green foliage, and a more upright plant habit.

The male parent of 'PEHY0004' is a proprietary, unpatented plant identified as '1864-12' with amethyst flowers, green foliage, less plant vigor, and bigger flower size. The seed was sown in December 2007 in Gilroy, Calif.

'PEHY0004' was selected as one flowering plant within the progeny of the stated cross in the March 2008 in a controlled environment in Gilroy, Calif.

The first act of asexual reproduction of 'PEHY0004' was accomplished when vegetative cuttings were propagated from the initial selection in March 2008 in a controlled environment in Gilroy, Calif.

BRIEF SUMMARY OF INVENTION

Horticultural examination of plants grown from cuttings of the plant initiated in March 2008, and continuing thereafter, has demonstrated that the combination of characteristics as herein disclosed for 'PEHY0004' are firmly fixed and are retained through successive generations of asexual reproduction.

'PEHY0004' has not been observed under all possible environmental conditions. The phenotype may vary significantly with variations in environment such as temperature, light intensity and day length.

Plant Breeder's Rights for this cultivar were applied for in Canada on Dec. 17, 2010, #10-7133 and in the Community Plant Variety Office on Oct. 15, 2010, #2010/2185. 'PEHY0004' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0004' with colors being as true as possible with an illustration of this type.

Figure 1:
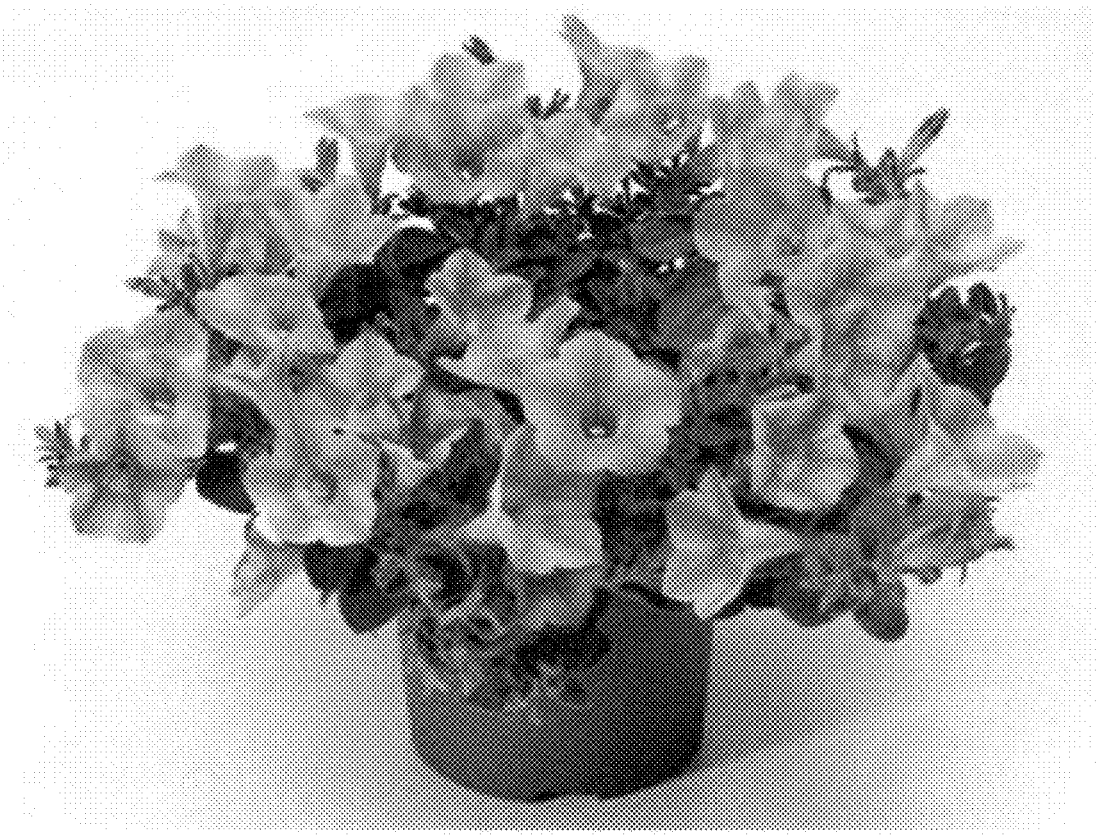
Figure 2:
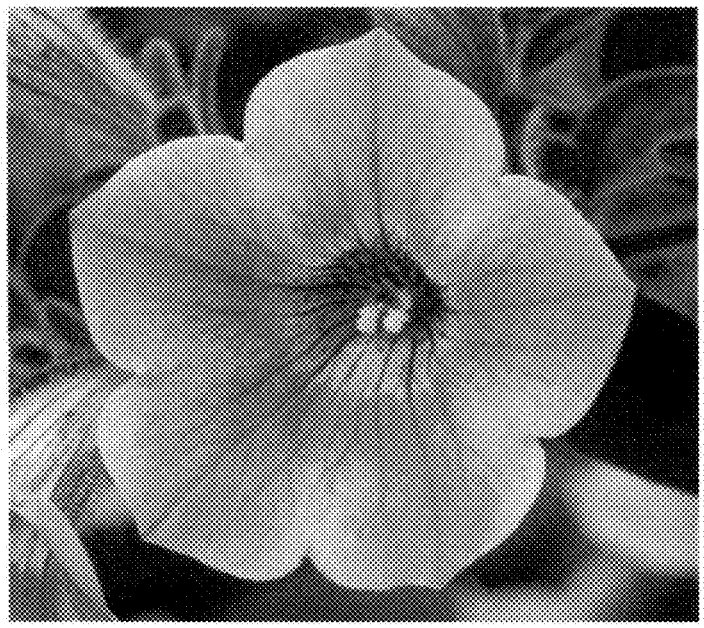

The photographic drawing shows in FIG. 1, a flowering plant of the new variety, and a close-up of the flowers in FIG. 2.

DETAILED BOTANICAL DESCRIPTION

The plant descriptions and measurements were taken in Gilroy, Calif. in April 2011 from plants growing in breeder trials in a greenhouse in 4 inch pots. These plants were approximately 9-10 weeks of age.

The aforementioned photographs were taken in April 2010 from plants grown in a greenhouse trial in Enkhuizen, The Netherlands. These plants were growing in 12 cm pots and were approximately 12 weeks of age.

Color references are made to The Royal Horticultural Society Colour Chart (R.H.S.) 2001.

TABLE 1

DIFFERENCES BETWEEN THE NEW VARIETY 'PEHY0004' AND A SIMILAR VARIETY

| | 'PEHY0004' | 'PIC ROSSA' (U.S. Plant Pat. No. 21,599) |
|---|---|---|
| Flower color: | Bi-colored | More solid |
| Plant habit: | More trailing | Much more compact |
| Vigor | More vigor | Less vigor |

Plant:

*Form, growth and habit.*—Initially semi-compact then more outwardly spreading, strong vigorous habit, well branched, small foliage, and continuously flowering.

*Plant height.*—5.0-6.0 cm.

*Plant height (inflorescence included).*—8.0-10.0 cm.

*Plant width.*—40.0-45.0 cm.

Roots:

*Number of days to initiate roots and produce a rooted cutting.*—18-23 days at about 22 degrees C.

*Type.*—Fine, fibrous, free branching.

*Color.*—RHS N155B but whiter.

Foliage:

*Arrangement.*—Alternate, upper leaves sub-opposite.

*Immature, leaf color, upper surface.*—Closest to RHS 137B with a silvery finish to it.

*Lower surface.*—Closest to RHS 138B.

*Mature, leaf color, upper surface.*—Closest to RHS 137A with a silvery finish to it.

*Lower surface.*—Closest to RHS 138B.

*Length.*—3.1-3.5 cm.

*Width.*—2.0-2.4 cm.

*Shape.*—Broadly elliptical.

*Base shape.*—Broadly acuminate.

*Apex shape.*—Obtuse.

*Margin.*—Entire.

*Texture, upper surface.*—Slightly hirsute; many glandular hairs.

*Lower surface.*—Slightly hirsute; many glandular hair.

*Color of veins, upper surface.*—RHS 144B becoming indistinct at margins and apex.

*Color of veins, lower surface.*—RHS 144B becoming indistinct at margins and apex.

*Petiole color.*—RHS 144B.

*Length.*—0.3-0.4 cm.

*Diameter.*—0.2-0.25 cm.

*Texture.*—Pilose; glandular hairs.

Stem:

*Color of stem.*—Closest to RHS 144A.

*Length of stem.*—About 25.0-30.0 cm.

*Diameter.*—0.25 cm.

*Length of internodes.*—3.0-4.5 cm.

*Texture.*—Heavily pilose; glandular hairs.

*Color of peduncle.*—RHS 144A.

*Length of peduncle.*—2.5-4.5 cm.

*Peduncle diameter.*—0.1 cm.

*Texture.*—Heavily pilose; glandular hairs.

Inflorescence:

*Type.*—Flowers appear solitary in upper leaf axis.

*Floret type.*—Funnel-shaped; 5 lobed petals; fused at the base; calyx, 5 deeply lobed sepals.

*Blooming habit.*—Continuous throughout the growing season. Good floriferousness.

*Quantity of inflorescences per plant.*—About 25 and many buds.

*Lastingness of individual blooms on the plant.*—About 5-7 days.

*Fragrance.*—None.

Bud (just when opening/showing color):

*Color.*—Closest to RHS 185D with hints of about RHS 182D in some inflorescence.

*Length.*—2.4-2.7 cm.

*Width.*—0.5 cm.

*Shape.*—Oblong.

Immature inflorescence:

*Diameter.*—About 3.5 cm.

*Color, upper surface.*—Ground color closest to RHS N66D, overlaid RHS N66B in a wide mottled pattern becoming darker around the throat; midveins and veining of about RHS N166A.

*Lower surface.*—Closest ground color to RHS 69D; between RHS 144A and RHS 144B mid-veins.

Mature inflorescence:

*Floret horizontal diameter.*—4.0-4.5 cm.

*Vertical depth.*—About 3.5 cm.

*Petal color, upper surface.*—Ground color closest to RHS N66D, overlaid RHS N66B in a wide mottled pattern becoming darker around the throat; mid-veins and veining of about RHS N166A. All becoming a lighter intensity when fully mature.

*Lower surface.*—Ground color closest to RHS 69D; mid-veins of between RHS 144A and RHS 144B.

*Petal apex shape.*—Slightly mucronulate.

*Petal base shape.*—Fused.

*Petal margin.*—Entire.

*Petal waviness.*—Slight.

*Petal lobation.*—Moderate.

*Petal texture, upper surface.*—Papillose.

*Under surface.*—Pilose; some glandular hairs especially on mid-veins.

*Corolla tube color inside.*—RHS N155D; heavily veined with RHS 59A with RHS 183A mid-veins.

*Outside.*—RHS N155D ground color with RHS N77B veining and RHS 144A mid-veins.

*Corolla tube length.*—About 2.5 cm.

*Corolla texture.*—Heavily pilose; glandular hairs.

Calyx:

*Color, upper surface.*—RHS 137C.

*Lower surface.*—RHS 138A but lighter.

*Length.*—1.1-1.3 cm.

*Width.*—0.2-0.4 cm.

*Shape.*—Lanceolate.

*Apex shape.*—Obtuse.

*Base.*—Fused.

*Margins.*—Entire.

*Texture, upper surface.*—Glandular hairs.

*Lower surface.*—Pilose; glandular hairs.

Reproductive organs:

*Pistil.*—1.

*Length.*—2.0-2.1 cm.

*Style color.*—RHS 144D.

*Style length.*—1.6 cm.

*Stigma color.*—RHS 146A with lighter margins.

*Ovary color.*—RHS 146A, lighter basally.

*Stamens.*—5.

*Color of filaments.*—RHS 157D with a hint of RHS 70B at the base of the anthers.

*Length filaments.*—1.2-1.8 cm.

*Anther color.*—RHS 155D.

*Anther length.*—0.15-0.2 cm.

*Anther shape.*—Oval.

*Color of pollen.*—RHS 155C.

*Pollen amount.*—Moderate.

*Fertility/seed set.*—Has not been observed on this hybrid.

*Disease/pest resistance.*—Has not been observed on this hybrid.

What is claimed is:

1. A new and distinct variety of *Petunia* plant named 'PEHY0004' substantially as illustrated and described herein.

* * * * *